US00PP37694P2

(12) United States Plant Patent
Barends

(10) Patent No.: US PP37,694 P2
(45) Date of Patent: Sep. 15, 2026

(54) ***BEGONIA* PLANT NAMED 'Dobegicfikidelso'**

(50) Latin Name: *Begonia hybrida*
Varietal Denomination: Dobegicfikidelso

(71) Applicant: DUMMEN GROUP B.V., De Lier (NL)

(72) Inventor: Eveline Barends, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/418,803

(22) Filed: Dec. 12, 2025

(51) Int. Cl.
*A01H 5/02* (2018.01)

(52) U.S. Cl.
USPC ..... Plt./343

(58) Field of Classification Search
USPC ..... Plt./343
CPC ..... A01H 6/185; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Begonia* plant named 'Dobegicfikidelso', characterized by its semi-upright and mounded plant habit; moderately vigorous growth habit and moderate growth rate; strong branching habit; dark green-colored leaves; freely and continuously flowering habit; and large double-type flowers with petals that are warm yellow in color that become closer to yellowish pink in color with subsequent development.

1 Drawing Sheet

Botanical designation: *Begonia hybrida.*
Cultivar denomination: 'DOBEGICFIKIDELSO'.

BACKGROUND OF THE INVENTION

The present invention relates to a new and distinct cultivar of *Begonia* plant, botanically known as *Begonia hybrida*, commonly referred to as a Hybrid *Begonia* and hereinafter referred to by the name 'Dobegicfikidelso'.

The new *Begonia* plant is a product of a planned breeding program conducted by the Inventor in De Lier, The Netherlands. The objective of the breeding program was to develop new freely flowering *Begonia* plants with strong branches and large yellow-colored flowers.

The new *Begonia* plant originated from a cross-pollination made by the Inventor during the autumn of 2013 of a proprietary selection of *Begonia hybrida* identified as code number BG14-000027-002, not patented, as the female, or seed, parent with a proprietary selection of *Begonia hybrida* identified as code number BG14-000027-005, not patented, as the male or pollen, parent. The new *Begonia* plant was discovered and selected by the Inventor as a single flowering plant from within the progeny of the stated cross-pollination in a controlled greenhouse environment in De Lier, The Netherlands in June, 2014.

Asexual reproduction of the new *Begonia* plant by vegetative tip cuttings in a controlled greenhouse environment in De Lier, The Netherlands since July, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegicfikidelso'. These characteristics in combination distinguish 'Dobegicfikidelso' as a new and distinct *Begonia* plant:

1. Semi-upright and mounded plant habit.
2. Moderately vigorous growth habit and moderate growth rate.
3. Strong branching habit.
4. Dark green-colored leaves.
5. Freely and continuously flowering habit.
6. Large double-type flowers with petals that are warm yellow in color that become closer to yellowish pink in color with subsequent development.

Plants of the new *Begonia* can be compared to plants of the female parent selection. In side-by-side comparisons, plants of the new *Begonia* differ primarily from plants of the female parent selection in flower color as flower petals of plants of the new *Begonia* are warm yellow in color and become closer to yellowish pink in color with subsequent development whereas flower petals of plants of the female parent selection are dark yellow and orangish red in color.

Plants of the new *Begonia* can be compared to plants of the male parent selection. In side-by-side comparisons, plants of the new *Begonia* differ primarily from plants of the male parent selection in branching habit as plants of the new *Begonia* are more freely branching, denser and bushier than plants of the male parent selection.

Plants of the new *Begonia* can be compared to plants of *Begonia boliviensis* X *Begonia tuberhybrida* 'I'CONIA Bacio Peach', not patented. In side-by-side comparisons, plants of the new *Begonia* differ primarily from plants of 'I'CONIA Bacio Peach' in the following characteristics:

1. Plants of the new *Begonia* are more upright and larger than plants of 'I'CONIA Bacio Peach'.
2. Plants of the new *Begonia* have larger leaves than plants of 'I'CONIA Bacio Peach'.

3. Fully expanded leaves of plants of the new *Begonia* are dark green in color whereas fully expanded leaves of plants of 'I'CONIA Bacio Peach' dark brownish green in color.
4. Flowers of plants of the new *Begonia* are fuller and have more petals and petaloids than flowers of plants of 'I'CONIA Bacio Peach'.
5. Flower petals of plants of the new *Begonia* are warm yellow in color and become closer to yellowish pink in color with subsequent development whereas flower petals of plants of 'I'CONIA Bacio Peach' are soft yellow to peach in color.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph is a side perspective view of a typical flowering plant of 'Dobegicfikidelso' grown in a container.

DETAILED BOTANICAL DESCRIPTION

Plants used for the aforementioned photograph and following observations and measurements were grown in 15-cm containers during the summer in a glass-covered greenhouse in De Lier, The Netherlands. During the production of the plants, day temperatures ranged from 20° C. to 35° C., night temperatures ranged from 15° C. to 25° C. and minium light levels were 135 watt/m$^2$. Plants were ten weeks old when the photograph was taken and twelve weeks old when the detailed description was taken. In the following description, color references are made to The Royal Horticultural Society Colour Chart, Fifth Edition, except where general terms of ordinary dictionary significance are used.

Botanical classification: *Begonia hybrida* 'Dobegicfikidelso'.

Parentage:

*Female, or seed, parent*.—Proprietary selection of *Begonia hybrida* identified as code number BG14-000027-002, not patented.

*Male, or pollen, parent*.—Proprietary selection of *Begonia hybrida* identified as code number BG14-000027-005, not patented.

Propagation:

*Type*.—By vegetative tip cuttings.

*Time to initiate roots, summer*.—About 20 days at temperatures about 22° C. to 30° C.

*Time to initiate roots, winter*.—About 24 days at temperatures about 22° C. to 30° C.

*Time to produce a rooted young plant, summer*.—About 25 days at temperatures about 22° C. to 30° C.

*Time to produce a rooted young plant, winter*.—About 28 days at temperatures about 20° C. to 25° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Semi-upright to mounded plant habit; freely basal branching with about five primary lateral branches each with about two secondary lateral branches; dense and bushy appearance; moderately vigorous growth habit and moderate growth rate.

*Plant height, soil level to top of foliar plane*.—About 25 cm.

*Plant height, soil level to top of floral plane*.—About 30 cm.

*Plant width*.—About 44 cm.

*Lateral branch description*.—Length: About 16 cm. Diameter: About 9 mm. Internode length: About 1.5 cm. Texture and luster: Pubescent; semi-glossy. Aspect: Mostly upright. Strength: Moderately strong, flexible. Color, developing: Close to 176C; at the internodes, close to 177B. Color, developed: Close to 152B; at the internodes, close to 177B.

*Leaf description*.—Arrangement: Alternate, single. Length: About 14.5 cm. Width: About 7 cm. Shape: Lanceolate. Apex: Narrowly acute. Base: Oblique. Margin: Serrate; sinuses medium in depth and divergent. Texture and luster, upper surface: Smooth, glabrous; semi-glossy. Texture and luster, lower surface: Pubescent; semi-glossy. Venation pattern: Palmate; reticulate. Color: Developing leaves, upper surface: Close to 178A. Developing leaves, lower surface: Close to 184B. Fully expanded leaves, upper surface: Close to 147A; venation, close to 147B. Fully expanded leaves, lower surface: Close to 184A; venation, close to 195A. Petioles: Length: About 8 cm. Diameter: About 3.5 mm. Texture and luster, upper and lower surfaces: Smooth, glabrous; semi-glossy. Strength: Moderately strong; flexible. Color, upper and lower surfaces: Close to 177A.

Flower description:

*Flowering habit*.—Double-type flowers arranged in axillary cymes; freely flowering habit with typically about two to three flowers per inflorescence and about 110 open flowers and flower buds per plant at one time; flowers face mostly upright to outwardly.

*Fragrance*.—None detected.

*Natural flowering season*.—Plants begin flowering about seven to eight weeks after planting; long flowering period, in the garden plants flower freely and continuously from the late spring throughout the summer in Northern Europe and can be flowered year-round in greenhouses under short nyctoperiods.

*Flower longevity*.—Depending on temperature, individual flowers last about four weeks on the plant; flowers persistent.

*Inflorescence height*.—About 6 cm.

*Inflorescence diameter*.—About 11.5 cm.

*Flower buds*.—Length: About 2.5 cm. Diameter: About 2.6 cm. Shape: Ovoid. Texture and luster: Smooth, glabrous; semi-glossy. Color: Close to 35B.

*Flower size*.—Diameter: About 7 cm. Depth (height): About 2.7 cm.

*Petals*.—Quantity per flower and arrangement: Typically 37 per flower arranged in about ten whorls. Length: About 3.8 cm. Width: About 3.4 cm. Shape: Obovate, rounded. Apex: Emarginate. Base: Cuneate. Margin: Entire; not undulate. Texture and luster, upper surface: Smooth, glabrous; matte. Texture and luster, lower surface: Smooth, glabrous; semi-glossy. Color: When opening, upper surface: Close to 16B. When opening, lower surface: Close to 37A. Fully opened, upper surface: Close to 13B; venation, close to 13B; color becoming closer to 32D with subsequent development. Fully opened, lower surface: Close to 8B; venation, close to 15C; color becoming close to 33D with subsequent development.

*Petaloids*.—Quantity per flower and arrangement: Typically about 41 per flower arranged in about seven whorls. Length: About 2.4 cm. Width: About 1.3 cm. Shape: Obovate. Apex: Retuse. Base: Cuneate. Margin: Entire; slightly undulate. Texture and luster, upper and lower surfaces: Smooth, glabrous; semi-glossy. Color: When opening, upper surface: Close to 7D. When opening, lower surface: Close to 2D. Fully opened, upper surface: Close to 7A; venation, close to 7A; color becoming closer to 7C with subsequent development. Fully opened, lower surface: Close to 7B; venation, close to 9B; color becoming closer to 9C with subsequent development.

*Sepals*.—Quantity per flower and arrangement: Typically two to five per flower arranged in one to two whorls. Length: About 3.9 cm. Width: About 3.7 mm. Shape: Obovate. Apex: Rounded and emarginate. Base: Cuneate and truncate. Margin: Entire. Texture and luster, upper and lower surfaces: Smooth, glabrous; semi-glossy. Color: When opening, upper surface: Close to 16B. When opening, lower surface: Close to 37A. Fully opened, upper surface: Close to 13B. Fully opened, lower surface: Close to 8B.

*Peduncles*.—Length: About 7.8 cm. Diameter: About 3 mm. Aspect: Semi-upright. Strength: Moderately strong; flexible. Texture and luster: Smooth, glabrous; glossy. Color: Close to 173A.

*Pedicels*.—Length: About 1.7 cm. Diameter: About 2 mm. Aspect: Upright to outwardly. Strength: Moderately strong; flexible. Texture and luster: Smooth, glabrous; glossy. Color: Close to N170B.

*Reproductive organs*.—Stamens: Quantity per flower: Ten or fewer. Filament length: About 7 mm. Filament color: Close to 145C. Anther length: About 1 mm. Anther shape: Oval. Anther color: Close to 145D. Pollen: Yellowish, close to 3C. Pistils: Quantity per flower: About three. Pistil length: About 1.8 cm. Stigma diameter: About 5 mm. Stigma shape: Bilobed, curled. Stigma color: Close to 17A. Style length: About 8 mm. Style color: Close to 17C. Ovary color: Close to 144B. Seeds: To date, plants of the new *Begonia* have not been observed to produce seeds Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 14° C. to about 30° C.

It is claimed:

1. A new and distinct *Begonia* plant named 'Dobegicfikidelso' as herein illustrated and described.

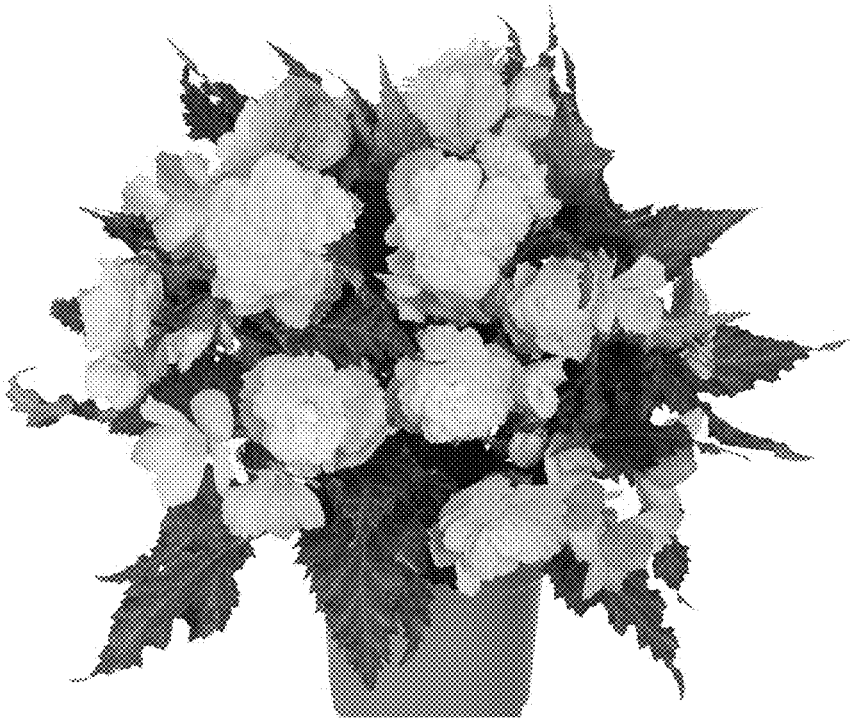

* * * * *